US012678564B2

(12) United States Patent
Davies et al.

(10) Patent No.: US 12,678,564 B2
(45) Date of Patent: Jul. 14, 2026

(54) TRAINING DEVICES AND METHODS FOR SIMULATING INTRANASAL DRUG DELIVERY

(71) Applicant: JANSSEN PHARMACEUTICA, N.V., Beerse (BE)

(72) Inventors: William Davies, East Lothian (GB); Ian Scrimgeour, East Lothian (GB); Nick Foley, Edinburgh (GB); Jimmy Mower, Edinburgh (GB); Monica A. Kapil, San Jose, CA (US)

(73) Assignee: Janssen Pharmaceutica, N.V., Beerse (BE)

( * ) Notice: Subject to any disclaimer, the term of this patent is extended or adjusted under 35 U.S.C. 154(b) by 1109 days.

(21) Appl. No.: 17/773,313

(22) PCT Filed: Oct. 30, 2020

(86) PCT No.: PCT/EP2020/080603
§ 371 (c)(1),
(2) Date: Apr. 29, 2022

(87) PCT Pub. No.: WO2021/084114
PCT Pub. Date: May 6, 2021

(65) Prior Publication Data
US 2022/0395636 A1      Dec. 15, 2022

Related U.S. Application Data

(60) Provisional application No. 62/929,279, filed on Nov. 1, 2019.

(51) Int. Cl.
*A61M 5/178*          (2006.01)
(52) U.S. Cl.
CPC ....... *A61M 5/178* (2013.01); *A61M 2205/582* (2013.01)

(58) Field of Classification Search
None
See application file for complete search history.

(56) References Cited

U.S. PATENT DOCUMENTS 6,321,942 B1      11/2001   Krampen et al.
6,446,627 B1 *    9/2002    Bowman ............... G06M 1/083
                                                      128/200.23

(Continued)

FOREIGN PATENT DOCUMENTS

EA          041066 B1     9/2022
GB          2566828 A     3/2019

(Continued)

OTHER PUBLICATIONS

International Search Report dated Jan. 29, 2021; International Application No. PCT/EP2020/080603.

(Continued)

*Primary Examiner* — Manuel A Mendez
(74) *Attorney, Agent, or Firm* — Craig M. Brown

(57)                    ABSTRACT

Various training devices and methods for simulating intra-nasal drug delivery are described. In one exemplary embodiment, a training device can include an outer sleeve, a locking sleeve coupled to the outer sleeve, a core sleeve coupled to the locking sleeve, and a plunger operatively coupled to the core sleeve. The plunger can be configured to selectively translate the core sleeve from an initial position to a first actuated position that indicates the release of a first simu-lated dose of a drug, and from the first actuated position to a second actuated position that indicates the release of a second simulated dose of the drug, in which the device does not contain the drug. The plunger can also be configured to rotate relative to the outer sleeve to reset the core sleeve to the initial position such that the core sleeve can be translated back to the first and second actuated positions.

26 Claims, 11 Drawing Sheets

(56)              References Cited

U.S. PATENT DOCUMENTS

| | | | |
|---|---|---|---|
| 7,299,949 | B2 | 11/2007 | Greiner-Perth |
| 8,062,264 | B2 * | 11/2011 | Godfrey .............. B05B 11/0032 |
| | | | 128/200.14 |
| 9,555,950 | B2 | 1/2017 | Le Maner et al. |
| 10,089,902 | B2 * | 10/2018 | Baker .................... G09B 19/24 |
| 2007/0111175 | A1 | 5/2007 | Raven et al. |
| 2010/0065049 | A1 | 3/2010 | Farieta et al. |
| 2010/0212663 | A1 | 8/2010 | Vedrine et al. |
| 2016/0068326 | A1 | 3/2016 | Le Maner et al. |
| 2018/0036482 | A1 | 2/2018 | Stefanov |
| 2018/0221588 | A1 | 8/2018 | Keitel |
| 2019/0251867 | A1 | 8/2019 | Baker et al. |
| 2020/0030539 | A1 | 1/2020 | Shabudin, Jr. |
| 2021/0027660 | A1 * | 1/2021 | Baker .................. G09B 23/285 |
| 2022/0395636 | A1 * | 12/2022 | Davies ................. A61M 5/178 |

FOREIGN PATENT DOCUMENTS

| | | | |
|---|---|---|---|
| GB | 2571625 | A8 | 9/2019 |
| WO | WO 2017/153077 | A1 | 9/2017 |
| WO | WO 2019/142007 | A1 | 7/2019 |

OTHER PUBLICATIONS

International Search Report and Written Opinion, received for PCT Application No. PCT/EP2020/080603, mailed on Jan. 29, 2021, 14 pages.

\* cited by examiner

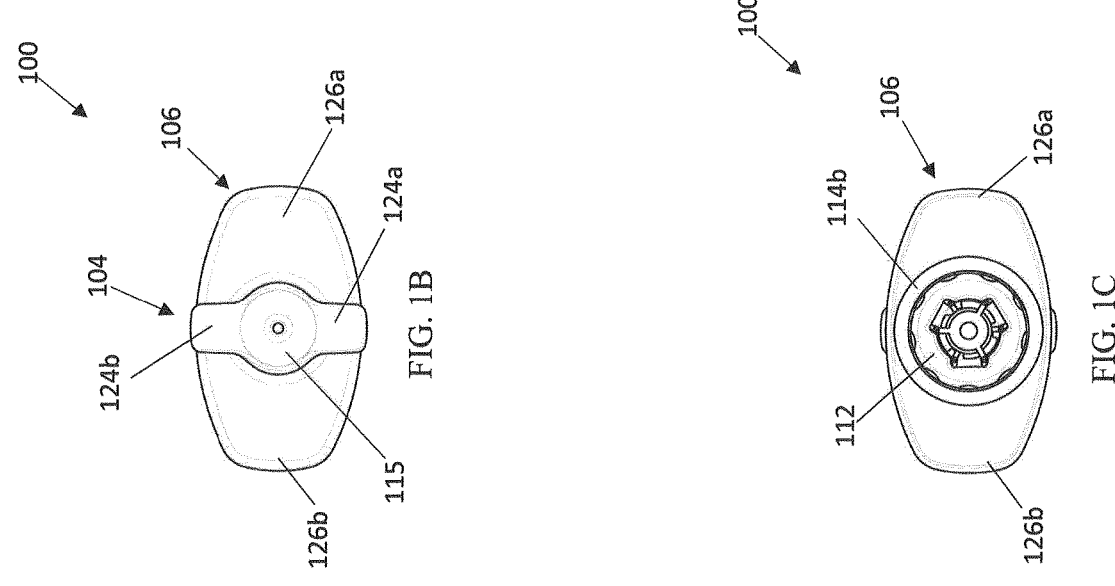
FIG. 1B
FIG. 1C
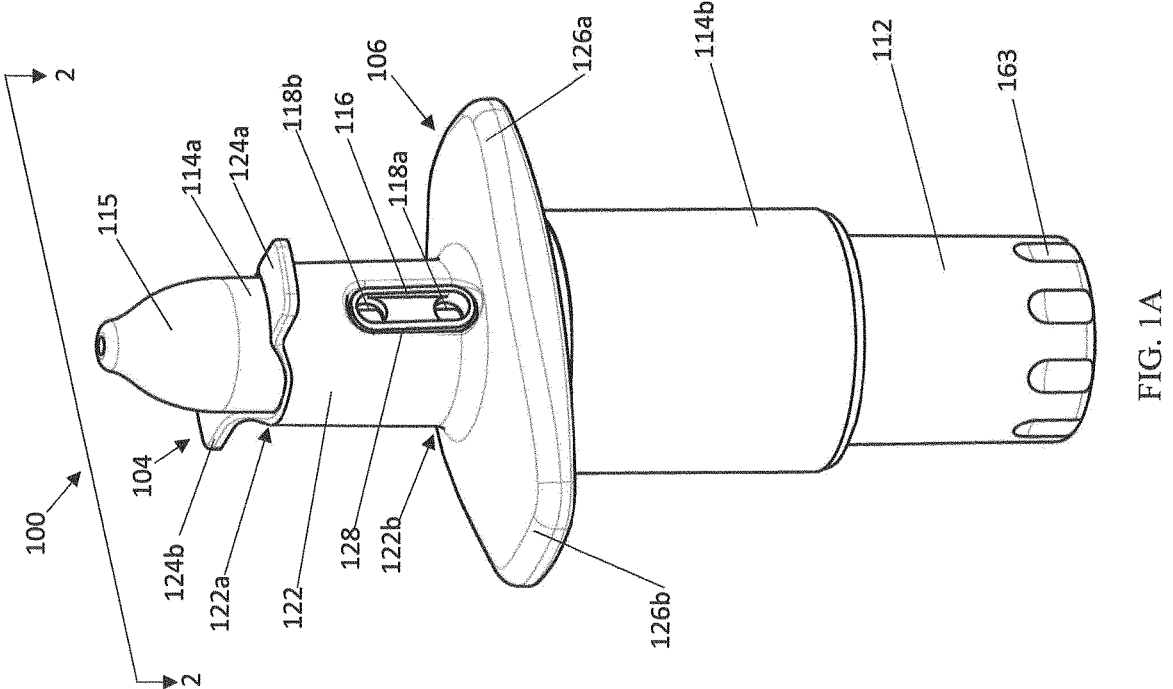
FIG. 1A

TRAINING DEVICES AND METHODS FOR SIMULATING INTRANASAL DRUG DELIVERY

CROSS REFERENCE TO RELATED APPLICATIONS

This application is the U.S. national stage of PCT Application No. PCT/EP2020/080603, filed Oct. 30, 2020, which claims priority to U.S. Provisional Patent Application No. 62/929,279, filed Nov. 1, 2019, the entire contents of each of which are hereby incorporated by reference in their entirety.

FIELD

Training devices and methods are disclosed for simulating intranasal drug delivery.

BACKGROUND

There are many different ways in which a drug can be administered to a user. Depending on the drug, intranasal drug delivery can be one of the most effective ways to achieve desired clinical benefits in a timely manner and in a manner that is convenient and comfortable for a patient.

Intranasal drug administration is a non-invasive route for drug delivery. Since the nasal mucosa offers numerous benefits as a target tissue for drug delivery, a wide variety of drugs may be administered by intranasal systemic action. Moreover, intranasal drug delivery can avoid the risks and discomfort associated with other routes of drug delivery (e.g., intravenous drug delivery), and can allow for easy self-administration.

Generally, to maximize the efficacy of the drug through intranasal administration, the majority volume of the aerosolized dose of the drug needs to reach the correct region of the nasal cavity. As such, additional measures may need to be taken for effective intranasal drug delivery. For example, the user may need to have a clear nostril; tilt their head back at approximately 45°; close the opposite nostril, and then sniff gently while the dose of drug is administered. In order to coordinate these measures, and given that nasal administration is intimate, self-administration by the user may be desired. Further, due to the nasal cycle (alternating physiological partial congestion of the nasal turbinate to facilitate nasal function) or pathological congestion, one nostril is likely to provide a more effective drug delivery route than the other nostril at any given time. As such, it is desired that an equal dose of the drug be delivered to each nostril of the user to inhibit under-dosing of the drug.

Dual-dose intranasal drug delivery devices are available that are designed for self-administration of two distinct aerosolized sprays, one for each nostril, that together constitute one dose of drug. These devices require a series of operational steps that the user needs to properly carry out to effect optimal drug delivery through self-administration. While users are typically provided with user manuals, commonly referred to as Instructions For Use (IFU), these manuals are limited in that they only graphically represent and textually describe the operational steps for using the device. As a result, prior to use, the user cannot have a tactile experience in using the device, which can lead to user misuse of the device, and thus ultimately inhibit effective drug delivery.

Accordingly, there remains a need for training devices that simulate the use of an intranasal drug delivery device without having to deliver any drug to the user.

SUMMARY

Various training devices and methods are disclosed for simulating intranasal drug delivery.

In one exemplary embodiment, a training device is provided and includes an outer sleeve having upper and lower portions, a locking sleeve coupled to the outer sleeve and partially extending therethrough, a core sleeve coupled to the locking sleeve and configured to axially slide within the outer and locking sleeves, the core sleeve having first and second sets of locking features, and a plunger operatively coupled to the core sleeve. The plunger is configured to selectively translate the core sleeve from an initial position to a first actuated position in response to the application of a first actuation force that exceeds a first force threshold, and configured to translate the core sleeve from the first actuated position to a second actuated position in response to the application of a second actuation force that exceeds a second force threshold, in which the first force threshold corresponds to a first spray threshold for releasing a first simulated dose of a drug and the second force threshold corresponds to a second spray threshold for releasing a second simulated dose of the drug, and the device does not contain the drug.

In some embodiments, the training device can include a protective hygiene cap that can be selectively mateable with and removable from the device.

The first and second sets of locking features can have a variety of configurations. For example, in some embodiments, the first sets of locking features can each include first and second flanges extending from an outer surface of the core sleeve and a first locking groove defined therebetween, in which the first locking groove can be configured to retain the core sleeve in the first actuated position. The second sets of locking features can each include third and fourth flanges extending from an outer surface of the core sleeve and a second locking groove defined therebetween, in which the second locking groove can be configured to retain the core sleeve in the second actuated position. In certain embodiments, the locking sleeve can include at least two snap arms, in which each snap arm has a protrusion extending from an inner surface thereof and toward the core sleeve, and each protrusion can be configured to engage the first locking groove when the core sleeve is in the first actuated position and configured to engage the second locking groove when the core sleeve is the second actuated position.

In some embodiments, the plunger can return to a start position after the application of the first actuation force and after the application of the second actuation force.

In some embodiments, the training device can include an indicator rod disposed within the upper portion of the outer sleeve. The indicator rod can be viewable through first and second indicator windows of the upper portion when the core sleeve is in the initial position. In such embodiments, the core sleeve can be configured to slide between indicator rod and the upper portion of the outer sleeve such that the core sleeve blocks the first indicator window when the core sleeve is in the first actuated position. In certain embodiments, the core sleeve can also block the first and second indicator windows when the core sleeve is in the second actuated position.

In another exemplary embodiment, a training device is provided and includes an outer sleeve having upper and lower portions, a locking sleeve coupled to the outer sleeve and partially extending therethrough, a core sleeve coupled to the locking sleeve and configured to axially slide within the outer and locking sleeves, the core sleeve having first and second sets of locking features, and a plunger operatively coupled to the core sleeve. The plunger is configured to selectively translate the core sleeve from an initial position to a first actuated position that indicates the release of a first simulated dose of a drug, and the plunger is configured to translate the core sleeve from the first actuated position to a second actuated position that indicates the release of a second simulated dose of the drug, in which the device does not contain a drug.

In some embodiments, the training device can include an indicator rod disposed within the upper portion of the outer sleeve. The indicator rod can be viewable through first and second indicator windows of the upper portion when the core sleeve is in the initial position. In such embodiments, the core sleeve can be configured to slide between the indicator rod and the upper portion of the outer sleeve such that the core sleeve blocks the first indicator window when the core sleeve is in the first actuated position to thereby indicate the release of the first simulated dose of the drug. In certain embodiments, the core sleeve can block the first and second indicator windows when the core sleeve is in the second actuated position to thereby indicate the release of the second simulated dose of the drug.

In some embodiments, the training device can include a protective hygiene cap that can be selectively mateable with and removable from the outer sleeve.

The first and second sets of locking features can have a variety of configurations. For example, in some embodiments, the first sets of locking features can each include first and second flanges extending from an outer surface of the core sleeve and a first locking groove defined therebetween, in which the first locking groove can be configured to retain the core sleeve in the first actuated position. The second sets of locking features can each include third and fourth flanges extending from an outer surface of the core sleeve and a second locking groove defined therebetween, in which the second locking groove can be configured to retain the core sleeve in the second actuated position. In certain embodiments, the locking sleeve can include at least two snap arms, in which each snap arm has a protrusion extending from an inner surface thereof and toward the core sleeve, and each protrusion can be configured to engage the first locking groove when the core sleeve is in the first actuated position and configured to engage the second locking groove when the core sleeve is the second actuated position.

In some embodiments, the plunger can return to a start position after the application of the first actuation force and after the application of the second actuation force.

In another exemplary embodiment, a training device is provided and includes an outer sleeve having upper and lower portions, a locking sleeve coupled to the outer sleeve and partially extending therethrough, a core sleeve coupled to the locking sleeve and configured to axially slide within the outer and locking sleeves, and a plunger operatively coupled to the core sleeve. The plunger is configured to axially translate relative to the outer sleeve to selectively slide the core sleeve in a first axial direction from a start position to a first axial position and from the first axial position to a second axial position, and the plunger is configured to rotate relative to the outer sleeve between an initial position and an actuated radial position, in which when the core sleeve is in the second axial position, rotation of the plunger from the initial position to the actuated radial position resets the core sleeve to the start position such that the core sleeve can axially translate back to the first and second axial positions.

In some embodiments, the training device includes a protective hygiene cap that is selectively mateable with and removable from the device.

In other embodiments, the core sleeve can be configured to be repeatedly reset.

In some embodiments, the training device can include a first biasing element that can bias the plunger to the initial position until a rotational force is applied to the plunger that overcomes a rotational biasing force of the first biasing element and thereby rotates the plunger in a first rotational direction. The release of the rotational force can allow the first biasing element to rotate the plunger in a second, opposite rotational direction to allow the plunger to return to the initial position. In certain embodiments, the training device can include a second biasing element that can bias the core sleeve to the start position until an axial force is applied to the core sleeve that overcomes an axial biasing force of the second biasing element and thereby translates the core sleeve in the first axial direction. In yet another embodiment, when the core sleeve is in the second axial position, rotation of the plunger in the first rotational direction can cause the core sleeve to rotate and disengage from the locking sleeve. Further, when the core sleeve is disengaged from the locking sleeve, the second biasing element can force the core sleeve in a second, opposite axial direction from the second axial position toward the start position. Further, a release of the rotational force can allow the first biasing element to rotate the plunger in a second, opposite rotational direction until the plunger reaches the initial position, and rotation of the plunger in the second rotational direction can rotate the core sleeve back to the start position.

Methods for simulating intranasal drug delivery are also provided. In one exemplary embodiment, the method can include depressing a plunger operatively coupled to a core sleeve of a training device to axially translate the core sleeve in a first axial direction from a start position to a first actuated position, the first actuated position being associated with the completion of the release of a first simulated dose of a drug, depressing the plunger to axially translate the core sleeve in the first axial direction from the first actuated position to a second actuated position, the second actuated position being associated with the completion of the release of a second simulated dose of the drug, and rotating the plunger to reset the core sleeve to the start position to thereby allow the core sleeve to axially translate back to the first and second actuated positions, in which the device does not contain a drug.

In some embodiments, the method can include, prior to depression of the plunger when the core sleeve is in the start position, inserting a portion of the device into a first nostril. In such embodiments, the method can include, prior to depression of the plunger when the core sleeve is in the first actuated position, removing the device from the first nostril and inserting the portion of the device into a second nostril.

In some embodiments, rotation of the plunger can include applying a rotational force to the plunger to rotate the plunger in a first rotational direction to thereby move the plunger from an initial radial position to an actuated radial position, and releasing the rotational force to allow the plunger to rotate in a second, opposite radial direction and return to the initial radial position.

In some embodiments, prior to depression of the plunger, an indicator rod disposed within an outer sleeve of the training device can be viewable through first and second indicator windows of the outer sleeve. In such embodiments, depressing the plunger to axially translate the core sleeve to the first actuated position can cause the core sleeve to translate in a distal direction between the indicator rod and the outer sleeve to thereby block the indicator rod from being viewable through the first indicator window to indicate the completion of the release of the first simulated dose of the drug. In such embodiments, depressing the plunger to axially translate the core sleeve to the second actuated position can cause the core sleeve to further translate in the distal direction between the indicator rod and the outer sleeve to thereby block the indicator rod from being viewable through the first and second indicator windows to indicate the completion of the release of the second simulated dose of the drug. In such embodiments, rotating the plunger can cause the core sleeve to translate back in a proximal direction between the indicator rod and the outer sleeve to thereby unblock the first and second indicator windows such that the indicator rod is viewable therethrough to indicate that the core sleeve is reset.

BRIEF DESCRIPTION OF THE DRAWINGS

This invention will be more fully understood from the following detailed description taken in conjunction with the accompanying drawings, in which:

FIG. 1A is an isometric view of one embodiment of a training device;

FIG. 1B is a top orthographic view of the training device of FIG. 1A;

FIG. 1C is a bottom orthographic view of the training device of FIG. 1A;

DETAILED DESCRIPTION

Figure 1D:
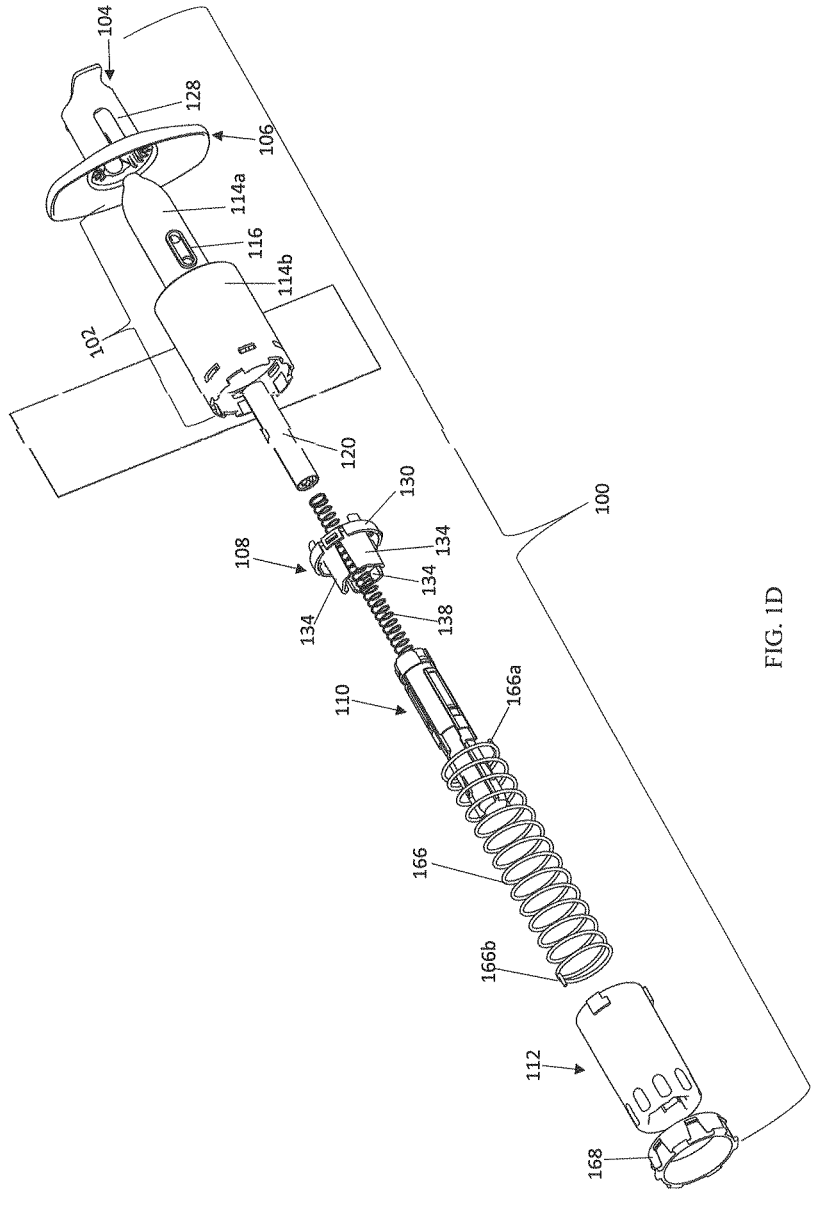
FIG. 1D is a partial exploded view of the training device of FIG. 1A.

Certain exemplary embodiments will now be described to provide an overall understanding of the principles of the structure, function, manufacture, and use of the training devices disclosed herein. One or more examples of these embodiments are illustrated in the accompanying drawings. Those skilled in the art will understand that the training devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various training devices and methods are provided for simulating intranasal drug administration without delivering drug to the user. As discussed in more detail below, unlike intranasal drug delivery devices, the training devices do not contain any drug. These devices are structurally configured to mimic multiple aspects of using an intranasal drug delivery device. The training devices are also designed for repeated use by either one user or multiple users. As a result, prior to using the intranasal drug delivery device, a user can use these training devices to learn and familiarize themselves with the operational steps and proper techniques needed to effectively use the intranasal drug delivery device.

The training devices generally include an outer sleeve, a locking sleeve, a core sleeve, and a plunger. As discussed in more detail below, the plunger selectively translates the core sleeve to a first actuated position that is associated with the release of a first simulated dose of a drug and further to a second actuated position that is associated with the release of a second simulated dose of the drug. The release of the first simulated dose and the second simulated dose correspond to the release of the first dose and the second dose of drug, respectively, from an intranasal drug delivery device. As a result, positioning and actuating the training devices provides the user with a similar tactile experience to that of positioning and actuating the intranasal drug delivery device. Further, repeated use of the training devices allows the user to develop a degree of muscle memory, which can be helpful in developing the proper use techniques of the intranasal drug delivery device. Thus, these training devices provide the user with the ability to practice, and consequently familiarize himself/herself with, the operational steps required for proper use of the intranasal drug delivery device to optimize drug delivery and drug efficacy, while also reducing waste and user anxiety.

In general, the training devices described herein are designed to carry out three stages of operation without expelling any drug to the user. The first and second stages of operation involve two separate actuations of the device, one corresponding to a first simulated dose of drug and the other corresponding to a second simulated dose of drug. These two separate actuations are similar in form, device positioning, and device actuation that is used to release a drug from a dual-dose intranasal drug delivery device. Further, unlike the dual-dose intranasal drug delivery devices, the training devices are not designed for a one-time use, but rather multiple uses, and therefore includes a third stage of operation to reset the device for subsequent simulated doses, either by the same user or different users. In particular, the training devices include a reset mechanism that can be activated after the completion of the second stage of operation to reset the device. As a result, a user can repeatedly use the training devices to simulate intranasal drug delivery without releasing any drug. Non-limiting exemplary embodiments of other suitable dual-dose intranasal drug delivery devices are described in more detail in U.S. Pat. Nos. 9,555,950, 7,299,949, and 6,321,942, each of which is hereby incorporated by reference in its entirety.

An exemplary training device can include a variety of features to facilitate simulation of intranasal drug delivery of a drug from a dual-dosed intranasal drug delivery device, as described herein and illustrated in the drawings. However, a person skilled in the art will appreciate that the training devices can include only some of these features and/or can include a variety of other features known in the art. The training devices described herein are merely intended to represent certain exemplary embodiments.

FIGS. 1A-2B illustrate an exemplary embodiment of a training device 100 that is configured to simulate intranasal drug delivery. The device 100 includes an outer sleeve 102, a depth guide 104, a finger rest 106, a locking sleeve 108, a core sleeve 110, and a plunger 112.

While the outer sleeve 102 can have a variety of configurations, the outer sleeve 102, as shown in FIG. 1D, includes upper and lower segments 114a, 114b. The upper and lower segments 114a, 114b each have a cylindrical structure. As shown, the upper segment 114a culminates in a tip 115. The tip 115 is configured to be inserted into a first nostril during the first stage of operation of the device 100 and a second nostril during the second stage of operation of the device 100. In other embodiments, the upper and lower segments 114a, 114b can have other suitable structural configurations.

As shown in FIGS. 1A, 1D and 2A-2B, the upper segment 114a of the outer sleeve 102 includes an indicator frame 116 that surrounds two indicator windows 118a, 118b. In this illustrated embodiment, the indicator frame 116 has an oblong-shaped configuration and the two indicator windows 118a, 118b each have a circular-shaped configuration. In other embodiments, the indicator frame 116 and the two indicator windows 118a, 118b can have other suitable shaped configurations. As further shown in FIGS. 1D and 2A-2B, an indicator rod 120 is disposed within the outer sleeve 102 and partially extends through the upper segment 114a such that it overlaps with the two indicator windows 118a, 118b. As explained in more detail below, the indicator rod 120 is visible through the two indicator windows 118a, 118b prior to actuation of the device 100. That is, the visibility of the indicator rod 120 through both of these indicator windows 118a, 118b indicates to the user that the device 100 is in the start position. Further, in some embodiments, the indicator rod 120 can have a first color that is different than the color of the upper segment 114a of the outer sleeve 102 so as to enhance the visibility of the indicator rod 120 through the indicator windows 118a, 118b. For example, prior to any actuation and when the device 100 is ready for use, the indicator windows 118a, 118b can show a color such as green. After the first actuation the indicator window 118a can show a different color such as white and after the second actuation the indicator window 118b can likewise show the color white.

As shown in FIGS. 1A, 1D and 2A-2B, the depth guide 104 is conjoined to the finger rest 106 via an elongated tubular body 122. The depth guide 104 includes a first set of opposing flanges 124a, 124b extending from a first end 122a of the elongated tubular body 122. The first set of opposing flanges 124a, 124b are configured to limit the insertion depth of the upper segment 114a of the outer sleeve 102 into a user's nostril. The finger rest 106 includes a second set of two opposing flanges 126a, 126b extending from a second, opposing end 122b of the elongated tubular body 122. The finger rest 106 acts as a positioning guide for fingers of a user, e.g., the index and middle fingers of a user, such that a user can grasp and hold the device 100 while depressing the plunger 112 toward the upper segment 114a of the outer sleeve 102 using their thumb. The elongated tubular body 122 includes an oblong shaped hole 128 that corresponds to the indicator frame 116 of the upper segment 114a of the outer sleeve 102. As such, when the elongated tubular body 122, and consequently the depth guide 104 and finger rest 106, are positioned about a portion of the upper segment 114a of the outer sleeve 102, as shown in FIG. 1A, the indicator frame 116 extends through the oblong-shaped hole 128 of the elongated tubular body 122 to retain its position.

The locking sleeve 108 has an annular collar 130 that is coupled between the upper and lower segments 114a, 114b of the outer sleeve 102, thereby forming a shoulder 132. This coupling engagement retains the locking sleeve 108 in an immobile position within the outer sleeve 102. The locking sleeve 108 also includes snap arms 134 extending proximally from the annular collar 130 and partially through the lower segment 114b of the outer sleeve 102. While the number of snap arms 134 can vary, in this illustrated embodiment, the locking sleeve 108 includes three snap arms 134 oriented parallel to and arranged equally about the longitudinal axis ($L_A$) of the device 100. Each snap arm 134 includes an inward-facing protrusion 136, only one of which is shown, that is configured to engage locking features on the core sleeve 110. As such, the snap arms 134 can simultaneously flex outwardly when a conical profile is forced upwardly towards the upper segment 114a of the outer sleeve 102 and over inward-facing protrusions 136.

Figures 2A, 2B:
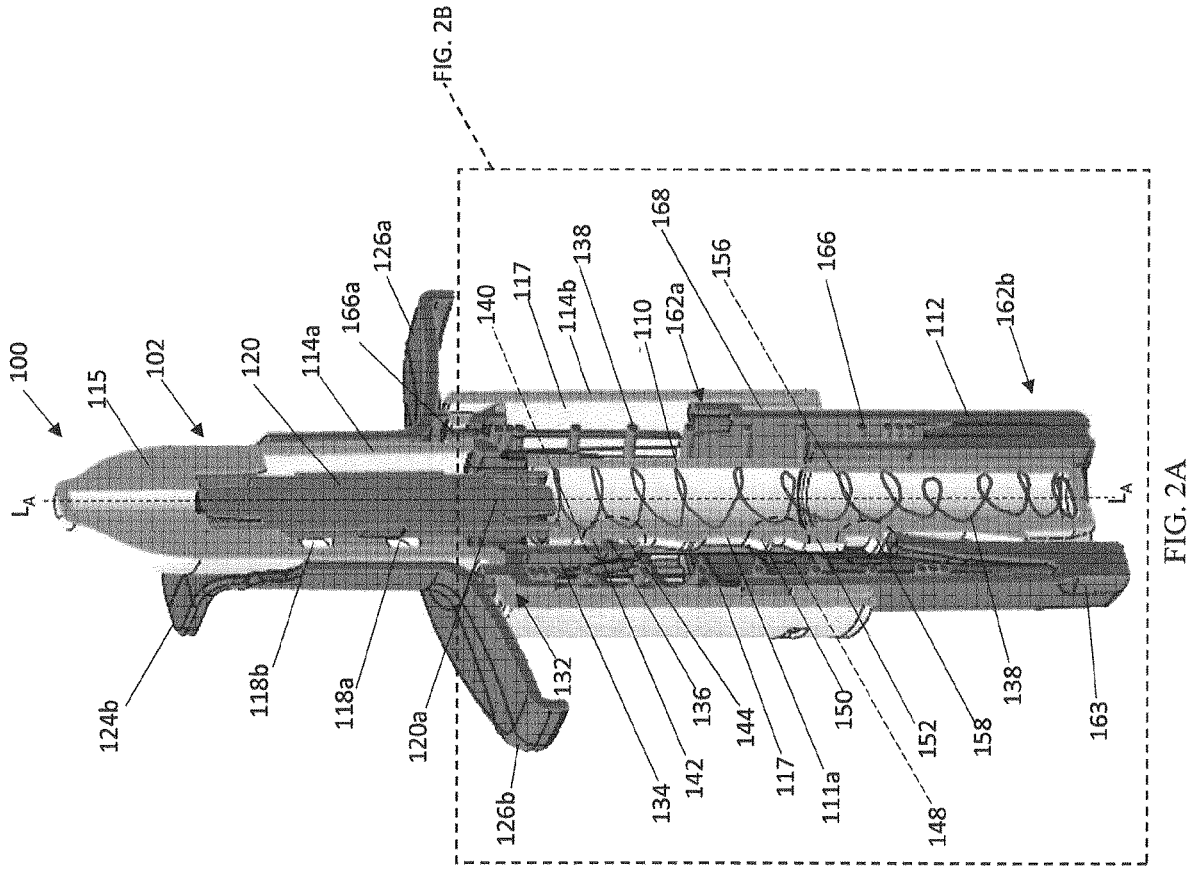
FIG. 2A is a cross-sectional view of the training device of FIG. 1A taken at 2-2.
FIG. 2B is a magnified cross-sectional view of a portion of the training device of FIG. 2A.
Figure 2B:
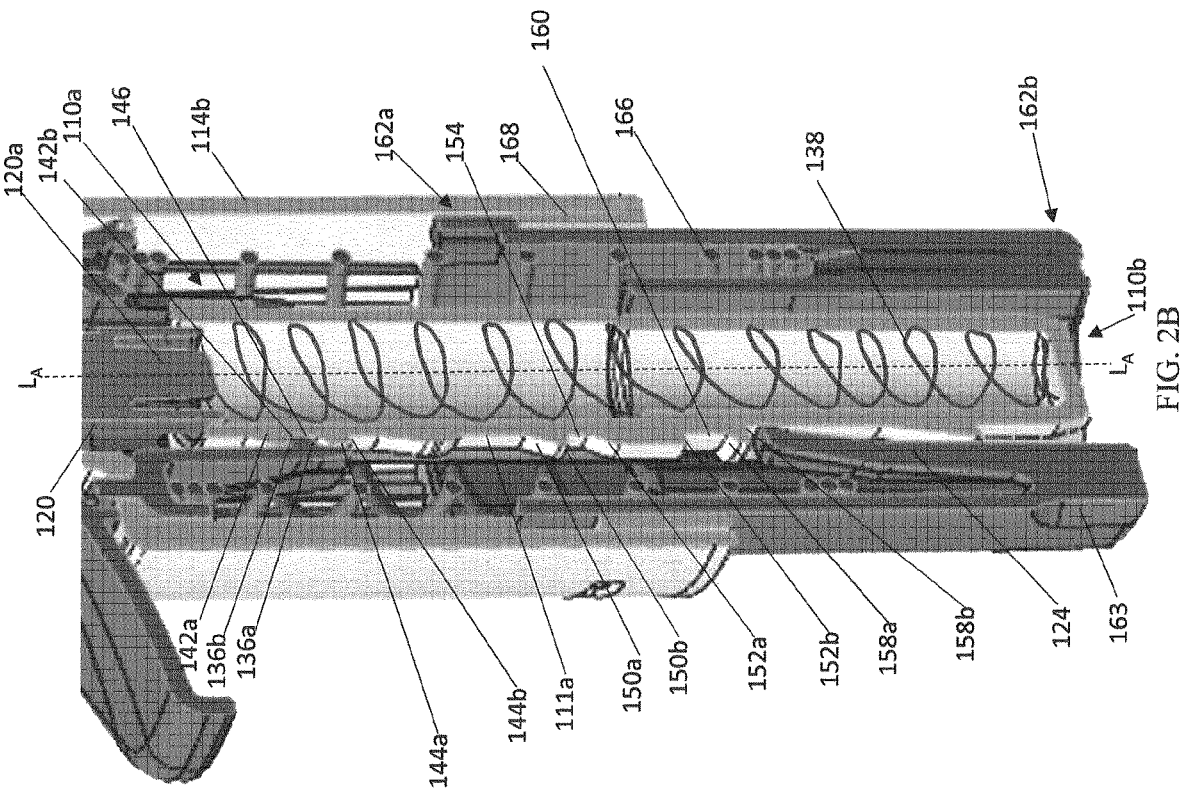

While the protrusions 136 can have a variety of configurations, as shown in FIGS. 1D and 2A-2B, the protrusions 136 each include at least a ramped surface 136a and a planar surface 136b. The planar surface 136b surface extends in a direction that is orthogonal to the longitudinal axis of the device 100. As will be discussed in more detail below, the ramped surface 136a of each protrusion 136 is configured to slide over flanges (such as second, third, and fourth flanges 144, 150, and 152) on the core sleeve 110 during the first and second stages of operation to allow for axial translation of the core sleeve 110 relative to the locking sleeve 108 and the planar surface 136b is configured to engage locking grooves (such as first, second, and third locking grooves 146, 154, and 160) on the core sleeve to lock the core sleeve in various positions.

Figure 3B:
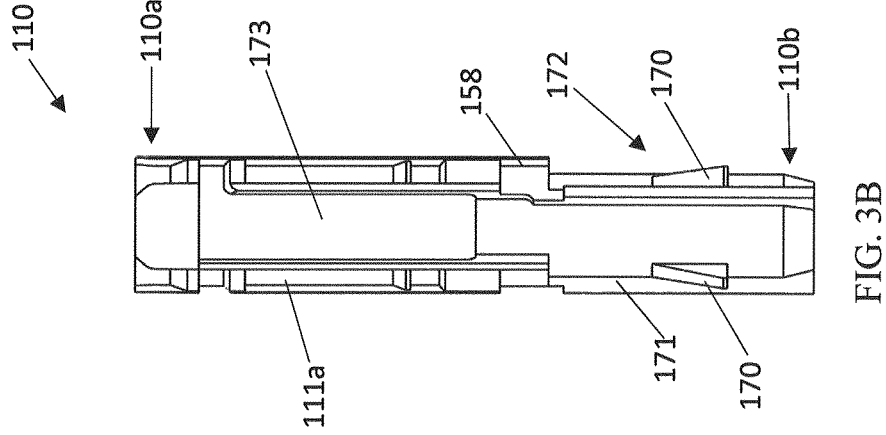
FIG. 3B is another side orthographic view of the core sleeve of the device of FIG. 1A.
Figure 3A:
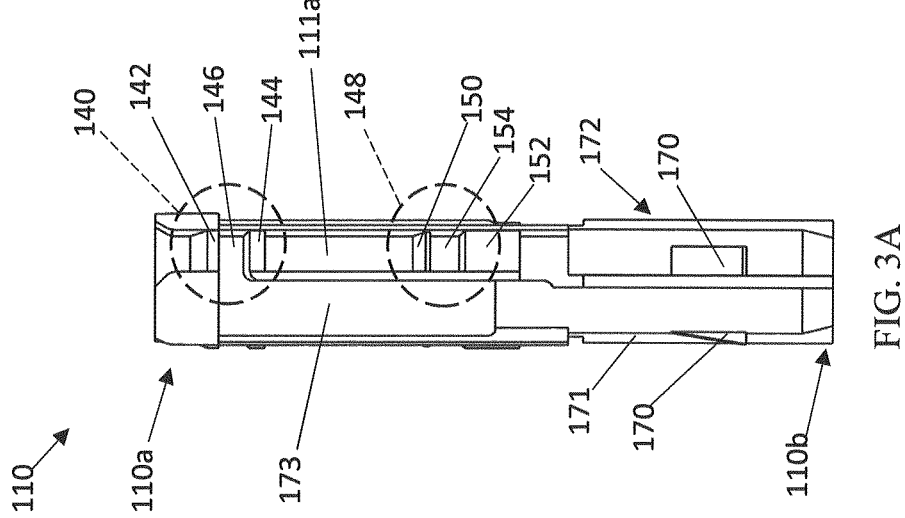
FIG. 3A is a side orthographic view of the core sleeve of the device of FIG. 1A.

As shown in FIGS. 1D and 2A-2B, and in more detail in FIGS. 3A and 3B, the core sleeve 110 extends from an open end 110a to a closed end 110b. A first biasing element 138 is retained within and compressed between the closed end 110b of the core sleeve 110 and an end 120a of the indicator rod 120. While the first biasing element 138 can have a variety of configurations, in this illustrated embodiment, the first biasing element 138 is a helical spring. The core sleeve 110 includes first sets of locking features 140. The first sets of locking features 140 in combination with the partial compression of the first biasing element 138 couples the core sleeve to the locking sleeve 108. Thus, the first biasing element 138 is configured to bias the core sleeve 110 to its initial position. As used herein, the term "initial position" is used synonymously with the term "start position."

The first sets of locking features 140 are positioned proximal to the open end 110*a* of the core sleeve 110. In this illustrated embodiment, the core sleeve 110 includes three first sets of locking features 140 that are substantially similar in structural configuration and configured to engage one corresponding protrusion 136 of one snap arm 134 of the locking sleeve 108. As such, for sake of simplicity, the following discussion is with respect to one of the first sets of locking features 140. A person skilled in the art will understand, however, that the following discussion is also applicable to the remaining first sets of locking features 140. Further, in other embodiments, the core sleeve 110 can include less than or greater than three first sets of locking features 140.

While the first set of locking features 140 can have a variety of structural configurations, the first set of locking features 140 as shown in FIGS. 2A-3B, includes first and second flanges 142, 144 extending from the outer surface 111*a* of the core sleeve 110 and a first locking grove 146 defined therebetween. As shown, the first and second flanges 142, 144 each include at least a ramped surface 142*a*, 144*a* and a planar surface 144*a*, 144*b*. The planar surface 144*a*, 144*b* extends in a direction orthogonal to the longitudinal axis of the device 100. The core sleeve 110 is therefore held in its start position by the first set of locking features 140 that interact with the protrusion 136 of the locking sleeve 108. That is, after assembling the device 100, the protrusion 136 of the locking sleeve 108 engages with the first locking groove 146 defined between the first and second flanges 142, 144 and is maintained in that position until a user actuates the device 100 during the first stage of operation.

Further, the ramped surface 142*a* of the second flange 144 has a ramp profile that is structurally designed such that during use, a certain amount of force needs to be applied to the core sleeve 110 before the ramp profile forces the snap arms 134 outwards at which point the core sleeve 110 can move freely towards the tip 115 of the device 100 and into a first actuated position. That is, the axial force (first actuation force) that is applied to the core sleeve 110 must exceed a first force threshold to allow the core sleeve 110 to be axially translated via the plunger 112 to a first actuated position. This first force threshold corresponds to a first spray threshold for releasing a first simulated dose of a drug from an intranasal drug delivery device. In one embodiment, the ramp profile can be engineered to match the first spray threshold of the intranasal drug delivery device ±20%.

The core sleeve 110 can include additional sets of locking features. For example, as shown in FIGS. 1D and 2A-2B, the core sleeve 110 includes second sets of locking features 148, which, as will be discussed in more detail, maintain the core sleeve 110 in a first actuated position. In this illustrated embodiment, the core sleeve 110 includes three second sets of locking features 148 that are substantially similar in structural configuration and configured to engage one corresponding protrusion 136 of one snap arm 134 of the locking sleeve 108. As such, for sake of simplicity, the following discussion is with respect to one of the second sets of locking features 148. A person skilled in the art will understand, however, that the following discussion is also applicable to the remaining second sets of locking features 148. Further, in other embodiments, the core sleeve 110 can include less than or greater than three second sets of locking features 148.

While the second set of locking features 148 can have a variety of structural configurations, the second set of locking features 148, as shown in FIGS. 2A-3B, includes third 150 and fourth flanges 152 extending from the outer surface 111*a* of the core sleeve 110 and a second locking groove 154 defined therebetween. As shown, the third 150 and fourth flanges 152 each include at least a ramped surface 150*a*, 152*a* and a planar surface 150*b*, 152*b*. The planar surface 150*b*, 152*b* extends in a direction that is orthogonal to the longitudinal axis ($L_A$) of the device 100. The core sleeve 110 is therefore held in a first actuated position by the second set of locking features 148 that interact with the protrusion 136 of the locking sleeve 108. That is, the protrusion 136 of the locking sleeve 108 engages with the second locking groove 154 defined between the third 150 and fourth flanges 152, and is maintained in that position until a user actuates the device 100 during the second stage of operation.

The ramped surface 150*a* of the third flange 150 has a ramp profile that is smaller than the ramp profile of the ramped surface 144*a* of the second flange 144. The smaller diameter of this ramp profile ensures that the user does not need to apply an increased force to the core sleeve 110 to slide over the ramped surface 150*a* of the third flange 150. That is, the first actuation force is sufficient to slide the core sleeve 110 from its initial position to its first actuated position.

Further, the ramped surface 152*a* of the fourth flange 152 has a ramp profile that is structurally designed such that during use, a certain amount of force needs to be applied to the core sleeve 110 before the ramp profile forces the snap arms 134 outwardly at which point the core sleeve 110 can move freely and further towards the tip 115 of the device 100 and into a second actuated position. That is, the axial force (second actuation force) applied to the core sleeve 110 must exceed a second force threshold to allow the core sleeve 110 to be axially translated via the plunger 112 to a second actuated position. This second force threshold corresponds to a second spray threshold for releasing a first simulated dose of a drug from an intranasal drug delivery device. In some embodiments, the second force threshold can be the same as the first force threshold, whereas in other embodiments, the second force threshold can be either greater than or less than first force threshold. For example, in one embodiment, the second force threshold is greater than the first force threshold. In one embodiment, the ramp profile can be engineered to match the second spray threshold of the intranasal drug delivery device ±20%.

The core sleeve 110 can also include third sets of locking features 156, which, as will be discussed in more detail, maintain the core sleeve 110 in a second actuated position. In this illustrated embodiment, the core sleeve 110 includes three third sets of locking features 156 that are substantially similar in structural configuration and configured to engage one corresponding protrusion of one snap arm 134 of the locking sleeve 108. As such, for sake of simplicity, the following discussion is with respect to one of the third sets of locking features 156. A person skilled in the art will understand, however, that the following discussion is also applicable to the remaining third sets of locking features 156. Further, in other embodiments, the core sleeve 110 can include less than or greater than three third sets of locking features 156.

While the third set of locking features 156 can have a variety of structural configurations, as shown in FIGS. 2A-3B, the third set of locking features 156 includes the fourth flange 152 and a fifth flange 158 extending from the outer surface 111*a* of the core sleeve 110 and a third locking grove 160 defined therebetween. As shown, the fifth flange 158 also includes at least a ramped surface 158*a* and a planar surface 158*b*. The planar surface 158*b* extends in a direction that is orthogonal to the longitudinal axis ($L_A$) of the device 100. The core sleeve 110 is therefore held in a second actuated position by the third set of locking features 156 that interact with the protrusion 136 of the locking sleeve 108. That is, the protrusion 136 of the locking sleeve 108 engages with the third locking groove 160 defined between the fourth and fifth flanges 152, 158, and is maintained in that position until a user resets the device 100 during the third stage of operation.

Figure 5:
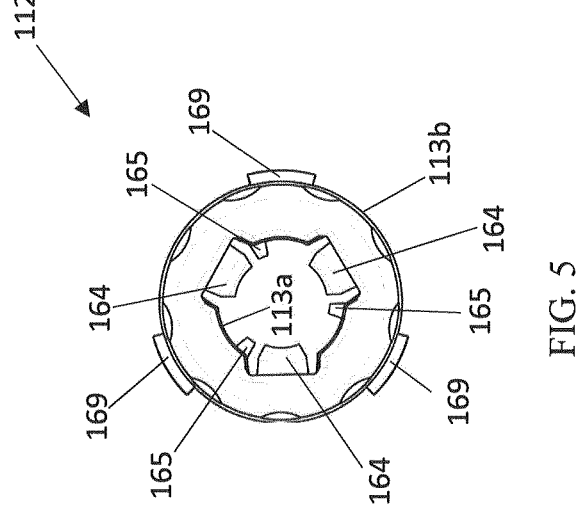
FIG. 5 is a bottom view of the plunger of FIG. 4.
Figure 4:
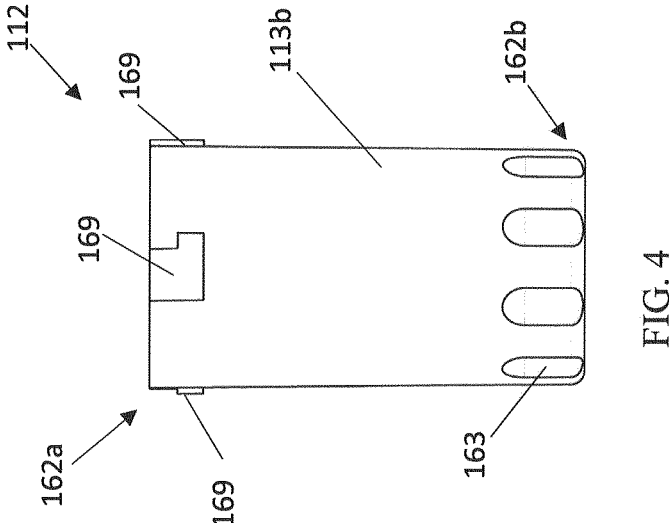
FIG. 4 is a side orthographic view of the plunger of the device of FIG. 1A.

Further, as shown in FIGS. 2A-2B, the plunger 112 is operatively coupled to the core sleeve 110 and configured to axially translate relative to the outer sleeve 102 to selectively slide the core sleeve 110 from its start position to its first actuated position and from its first actuated position to its second actuated position during the first and second stages of operation of the device 100, respectively. The plunger 112 is also configured to rotate relative to the outer sleeve 102 between an initial radial position and an actuated radial position to reset the device 100 after completion of the second stage of operation. While the plunger 112 can have a variety of configurations, the plunger 112, in this illustrated embodiment has an elongated tubular configuration extending from a first end 162*a* to a second end 162*b*. The plunger 112 also includes three equally spaced cantilever arms 164, as shown in FIG. 5. The cantilever arms 164, two of which are obstructed in FIGS. 2A-2B, are arranged radially from the first end 162*a* of the plunger 112 and extending towards the core sleeve 110. The plunger 112 can also include gripping features 163 to aid in rotation of the plunger 112, as shown in FIGS. 1A, 2A-2B, and 4.

A second biasing element 166 sits partially within the lower segment 114*b* of the outer sleeve 102, surrounding the locking and core sleeves 108, 110. While the second biasing element 166 can have a variety of configurations, in this illustrated embodiment, the second biasing element 166 is a helical spring. The ends 166*a*, 166*b* of this second biasing element 166 are each configured as a short tail that is parallel to the longitudinal axis ($L_A$) of the device 100. As shown, the first end 166*a* interacts with the shoulder 132 formed by the annular collar 130 of the locking sleeve 108 and the upper and lower segments 114*a*, 114*b* of the outer sleeve 102 such that the second biasing element 166 cannot freely rotate about the longitudinal axis of the device 100.

As shown in FIGS. 2A-2B, the plunger 112 is fitted over and partially compresses the second biasing element 166. While not shown, during assembly, the second end 166*b* of the second biasing element 166 engages with a rib on the inner surface 113*a* of the plunger 112. As a result, when the plunger 112 is fitted over the second biasing element 166, it is rotated clockwise about the longitudinal axis ($L_A$) of the device 100, thereby applying torsion to the second biasing element 166. As such, the second biasing element 166 biases the plunger 112 to an initial radial position, as shown in FIGS. 2A-2B.

Further, the plunger 112 is partially disposed within the lower segment 114*b* of the outer sleeve 102 and coupled thereto by a locking ring 168. The plunger 112, as shown in more detail in FIG. 4, includes three equally-spaced lugs 169 on outer surface 113*b* of the plunger 112 and positioned at the second end 112*b* of the plunger 112. The three lugs 169 each have a L-shaped configuration (see FIG. 4). As further shown in FIG. 5, the plunger 112 also includes three equally spaced axially-aligned rib features 165 on the inner surface 113*a* of the plunger 112. These rib features 165 are configured to engage corresponding rib features 171 on the core sleeve 110 such that the plunger 112 and the core sleeve 110 rotate together during a portion of the third stage of operation. As discussed below, this engagement allows the core sleeve 110 to disengage from, and rotate relative to, the locking sleeve 108 during a portion of the third stage of operation.

The plunger 112 is partially disposed within the lower segment 114*b* of the outer sleeve 102 so that the three lugs 169 are positioned within corresponding, axially-aligned channels 117, two of which are shown in FIG. 2A, on the inner surface of the lower segment 114*b* of the outer sleeve 102. As a result, during use, the plunger 112 can be depressed axially so that the three lugs 169 run along the channels 117 as the second biasing element 166 is compressed. Further, when the plunger 112 is in its initial radial position, it can be rotated in a first rotational direction to a limited degree, thereby applying further torque to the second biasing element 166. The second biasing element 166 therefore serves a dual purpose of returning the plunger 112 axially after each depression during the first and second stages of device operation, and also returning it radially after rotation during the third stage of the device operation.

Figures 6A, 6B, 6C:
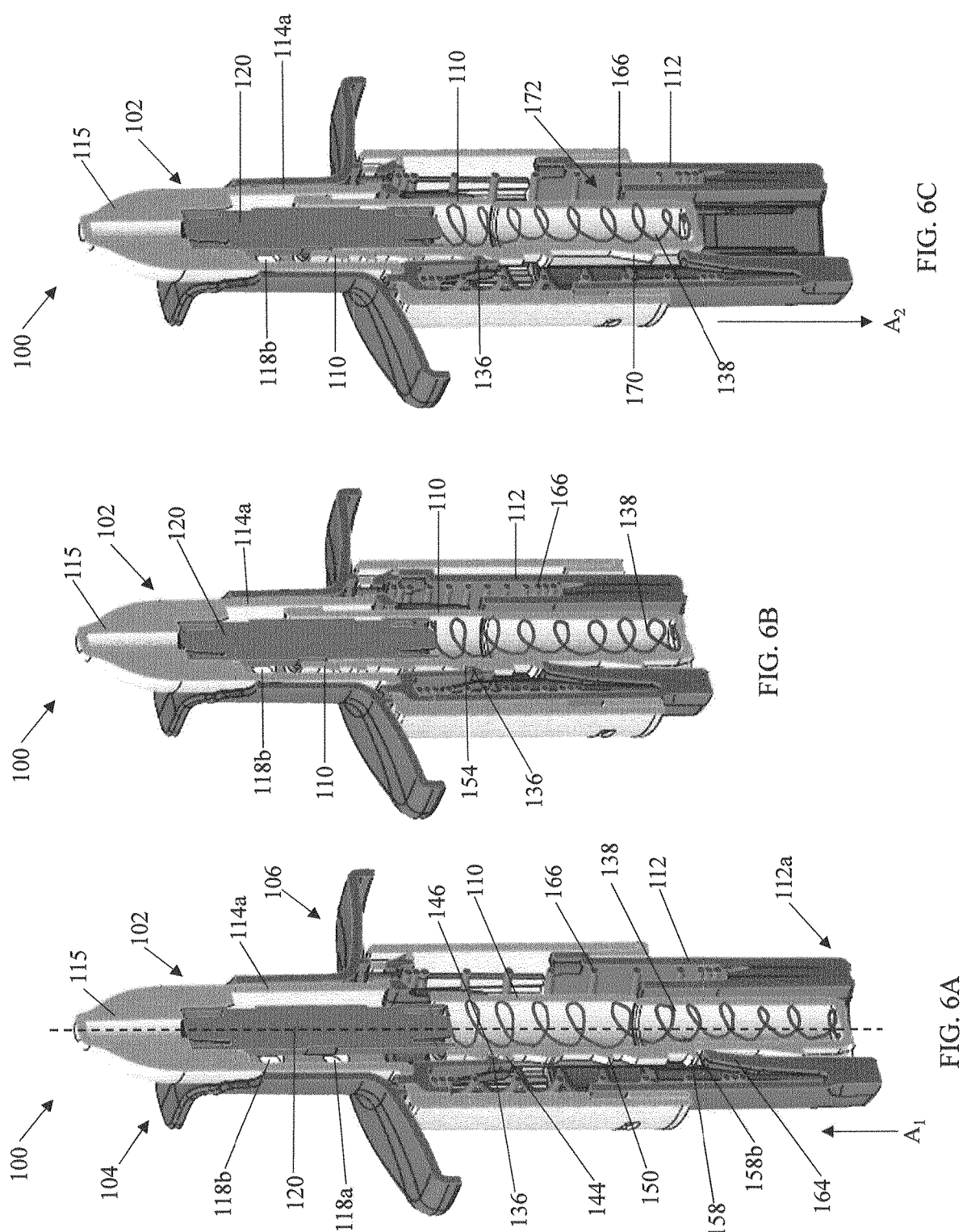
FIG. 6A is the device of FIG. 1A in a start position, showing the core sleeve and plunger each in an initial position.
FIG. 6B is the device of FIG. 6A during a first stage of operation, showing the core sleeve in a first actuated position that corresponds to the release of a first simulated dose of drug.
FIG. 6C is the device of FIG. 6B at the end of the first stage of operation, showing the return of the plunger to its initial position once the core sleeve is in the first actuated position.
Figure 6E:
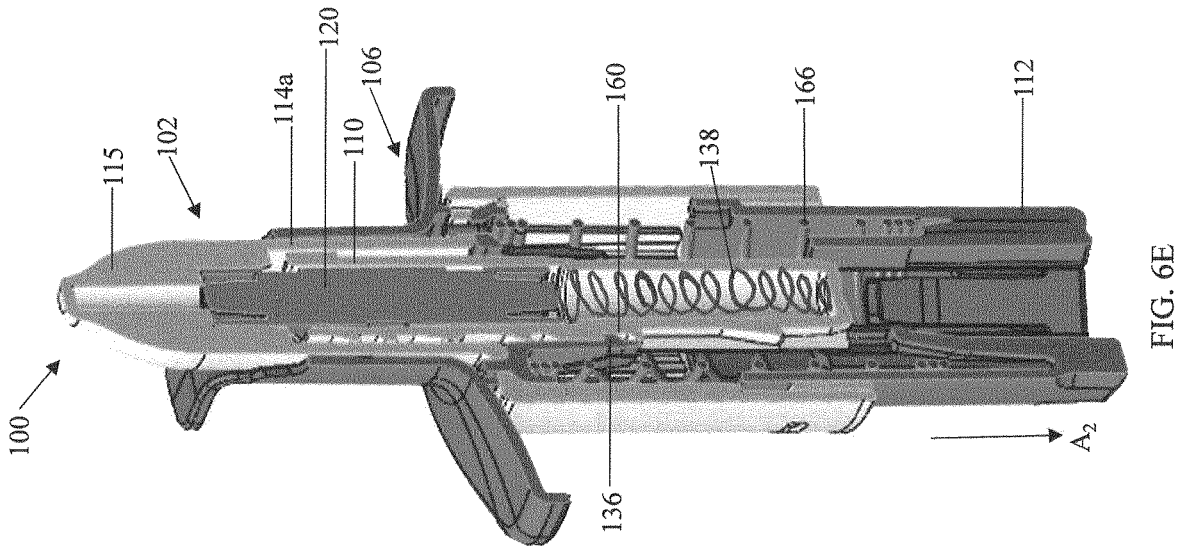
FIG. 6E is the device of FIG. 6D at the end of the second stage of operation, showing the core sleeve in the actuated position and the return of the plunger to its initial position.
Figure 6D:
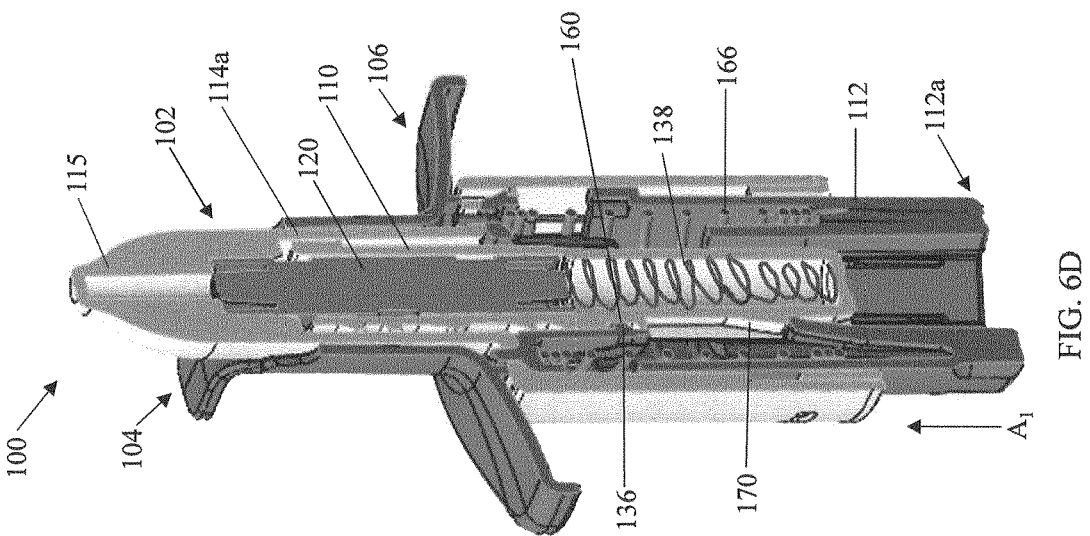
FIG. 6D is the device of FIG. 6A during a second stage of operation following the first stage of operation, showing the core sleeve in a second actuated position that corresponds to the release of a second simulated dose of drug.
Figures 7A, 7B, 7C:
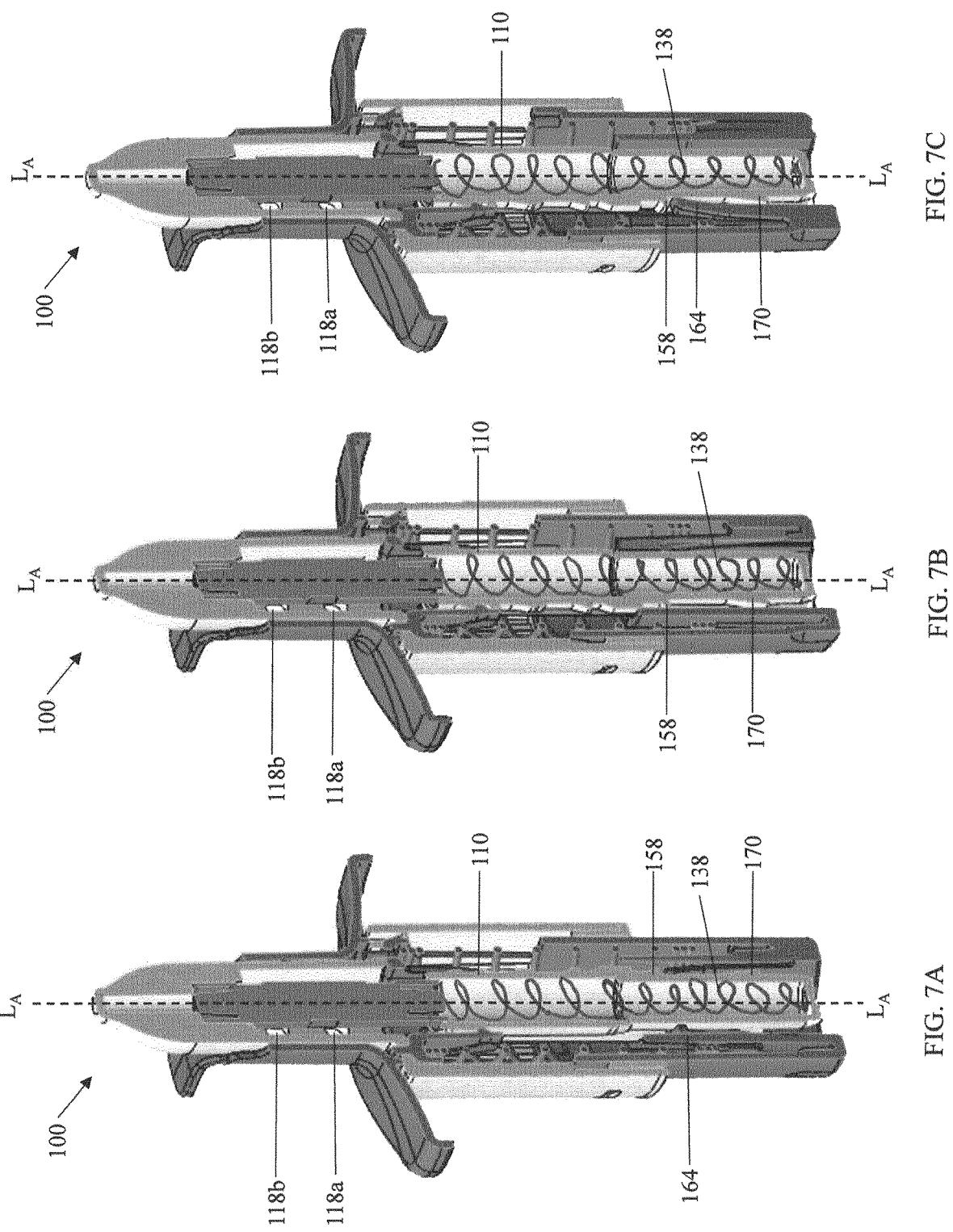
FIG. 7A is the device of FIG. 6A in a third stage operation following the second stage of operation, showing the plunger rotated towards an actuated radial position and the core sleeve disengaged from the lock sleeve and axially translated towards its initial position.
FIG. 7B is the device of FIG. 6A in the third stage of operation, showing the plunger further rotated and in its actuated radial position.
FIG. 7C is the device of FIG. 6A at the end of the third stage of operation, showing the return of the plunger and the core sleeve to their initial positions and the device reset to its start position.

As mentioned above, the training device 100 has three stages of operation, in which the first stage of operation is illustrated in FIGS. 6A-6C, the second stage of operation is illustrated in FIGS. 6D and 6E, and the third stage of operation is illustrated in FIGS. 7A-7C. In general, the first stage of operation involves axial translation of the core sleeve 110 to mimic a first spray of a drug from an intranasal drug delivery device, the second stage of operation involves further axial translation of the core sleeve 110 to mimic a second spray of the drug from the intranasal drug delivery device, and the third stage of operation involves rotation of the plunger 112 to axially reset the device 100, and thus the core sleeve 110, to its starting position for reuse. Each stage of operation is described in more detail below.

While not shown, prior to the first stage of operation, a user inserts the tip 115 of the outer sleeve 102 into their first nostril until the depth guide 104 contacts the skin between their first and second nostrils, such that the longitudinal axis ($L_A$) of the device 100 is aligned with the axis of the first nostril. Further, prior to insertion, in some embodiments, the user can tilt their head about 45 degrees relative to their neck.

During the first stage of operation, the user applies a first actuation force to the first end 112*a* of the plunger 112 in an axial direction ($A_1$) toward the upper segment 114*a* of the outer sleeve 102. The user can apply this force with their thumb in opposition to their fingers on the finger rest 106. This applied force first causes the cantilever arms 164 of the plunger 112 to push against the planar surface 158*b* of the fifth flange 158 on the core sleeve 110. Once the applied force exceeds a first threshold force, the plunger 112 axially translates the core sleeve 110 from its start position (FIG. 6A), in which the protrusions 136 of the locking sleeve 108 are engaged with the first locking groove 146 of the core sleeve 110, to a first actuated position (FIGS. 6B and 6C), in which the protrusions 136 of the locking sleeve 108 are engaged with the second locking groove 154 of the core sleeve 110. This applied force therefore causes the protrusions 136 of the locking sleeve 108 to slide along the second and third flanges 144, 150 and snap into engagement with the second locking groove 154 of the core sleeve 110. As a result, the first biasing element 138 is further compressed from an initial compressed position (FIG. 6A) to a first compressed position (FIGS. 6B and 6C).

Further, during this translation, the core sleeve 110 slides between the indicator rod 120 and the upper segment 114*a* of the outer sleeve 102. As a result, when the core sleeve 110 is in the first actuated position (FIGS. 6B and 6C), the core sleeve 110 blocks the first indicator window 118*a* thereby indicating the release of the first simulated dose of the drug. Once the core sleeve 110 has reached its first actuated position, the user can release the plunger 112 and allow the second biasing element 166 to push the plunger 112 back in a reverse axial direction ($A_2$) to its start position (FIG. 6C). As the plunger 112 returns to its start position, the three cantilever arms 164 ride over a set of three ramped protrusions 170 on a lower section 172 of the core sleeve 110.

While not shown, prior to the second stage of operation, a user removes the tip 115 from their first nostril and inserts the tip 115 of the outer sleeve 102 into their second nostril until the depth guide 104 contacts the skin between their first and second nostrils, such that the longitudinal axis ($L_A$) of the device 100 is aligned with the axis of the second nostril. Further, prior to insertion, in some embodiments, the user can tilt their head about 45 degrees relative to their neck (e.g., 45 degrees backwards from a user's vertical).

During the second stage of operation, the user applies a second actuation force to the first end 112*a* of the plunger 112 in the axial direction ($A_1$) toward the upper segment 114*a* of the outer sleeve 102. The user can apply this force with their thumb in opposition to their fingers on the finger rest 106. This applied force first causes the cantilever arms 164 of the plunger 112 to push against the three ramped protrusions 170 on the core sleeve 110. Once the second applied force exceeds the second threshold force, the plunger 112 axially translates the core sleeve 110 from its first actuated position (FIGS. 6B and 6C), in which the protrusions 136 of the locking sleeve 108 are engaged with the second locking groove 154 of the core sleeve 110, to its second actuated position (FIG. 6D), in which the protrusions 136 of the locking sleeve 108 are engaged with the third locking groove 160 of the core sleeve 110. This applied force therefore causes the protrusions 136 of the locking sleeve 108 to slide along the fourth flange 152 and snap into engagement with the third locking groove 160. As a result, the first biasing element is further compressed from its first compressed position (FIGS. 6B and 6C) to a second compressed position (FIGS. 6D and 6E).

Further, during this translation, the core sleeve 110 further slides between the indicator rod 120 and the upper segment 114*a* of the outer sleeve 102. As a result, when the core sleeve 110 is in the second actuated position, the core sleeve 110 blocks both the first and second indicator windows 118*a*, 118*b* such that the indicator rod 120 is not visible. This indicates the release of the second simulated dose of the drug, and thus the completion of both simulated doses. Once the core sleeve 110 has reached its second actuated position, the user can release the plunger 112 and allow the second biasing element 166 to push the plunger 112 back in a reverse axial direction to its start position (FIG. 6E).

Once the outer sleeve 102 is removed from the second nostril, the user can carry out the third stage of operation. The third stage of operation resets the device 100. Once the core sleeve 110 is in the second actuated position, the plunger 112 can be rotated about the longitudinal axis ($L_A$) of the device 100 relative to the outer sleeve 102 (e.g., in a clockwise direction when viewed from the first end 162*a* of the plunger 112), and thus against the torque of the second biasing element 166.

During the third stage of operation, in which the core sleeve 110 begins in the second actuated position, rotation of the plunger 112 about the longitudinal axis ($L_A$) of the device 100 resets the core sleeve 110 to the start position such that the core sleeve 110 can axially translate back to the first and second actuated positions. In this illustrated embodiment, the actuated radial position of the plunger 112 can be achieved by rotating the plunger 112 by a certain amount, such as about 120 degrees from its initial radial position. In other embodiments, the actuated radial position of the plunger 112 can be achieved by rotating the plunger 112 about 90 degrees from its initial radial position, or by an amount between 90-120 degrees. A person skilled in the art will appreciate that any amount of rotation to rotate the plunger 112 from its initial radial position to its actuated radial position may be possible and depends at least upon the structural configurations of the locking sleeve 108, the core sleeve 110, and the plunger 112.

During the third stage of operation, a rotational force is applied to the plunger 112 that exceeds a rotational biasing force (torque) of the second biasing element 166 to thereby rotate the plunger 112 in a first rotational direction relative to the outer sleeve 102 (e.g., a clockwise direction) when viewed from the first end of the plunger 112 from its initial radial position to its actuated radial position. After a first degree of rotation of the plunger 112 (e.g., about 40 degrees) towards its actuated radial position (FIG. 7A), the cantilever arms 164 are rotated such that they are out of axial alignment with the fifth flange 158 and the three ramped protrusions 170 on the core sleeve 110. Also at this point of rotation, the three rib features 165 of the plunger 112 (see FIG. 5) make contact with the three rib features 171 on the core sleeve 110 (see FIGS. 3A-3B). As a result, the plunger 112 and the core sleeve 110 concurrently rotate through the second degree of rotation (e.g., about 50 degrees) until the plunger 112 reaches its actuated radial position (FIG. 7B). During this second degree of rotation, the core sleeve 110 rotates relative to the locking sleeve 108 such that the protrusions 136 of the locking sleeve 108 move into axially-aligned channels 173 (see FIGS. 3A-3B) on the core sleeve 110. This allows the first biasing element 138 to push the core sleeve 110 back in a second, axial direction towards its start position. At this point, the indicator rod 120 is now visible through both indicator windows 118*a*, 118*b* of the upper segment 114*a* of the outer sleeve 102. When the plunger 112 is released, the second biasing element 166 rotates the plunger 112 in a second, opposing rotational direction so that the plunger returns to its initial radial position, and during this rotation the plunger 112 rotates the core sleeve 110 back to its start position (FIG. 7C).

In some embodiments, the indicator rod 120 can be a different color than the core sleeve 110 so as to aid the user in visually verifying the position of the core sleeve 110. That is, the difference in color of the indicator rod and the core sleeve can help visually indicate to the user that the core sleeve is in the start position, the first actuated position, and the second actuated positions.

Once the user becomes familiar with using the training device 100, the training device 100 can be disposed. As such, the training device 100 is configured to be used multiple times by a single user. In other embodiments, the training device 100 can be configured to be used multiple times by multiple users.

Figure 8:
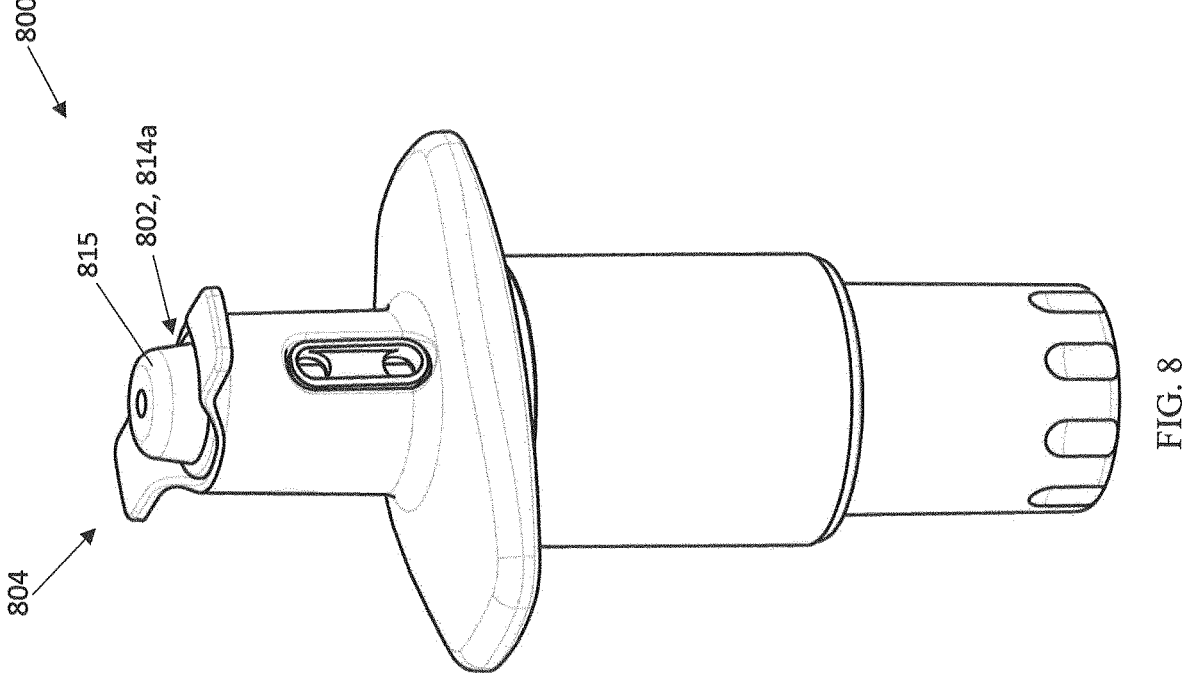
FIG. 8 is an isometric view of another embodiment of a training device.

FIG. 8 illustrates another exemplary embodiment of a training device 800 that can be used multiple times by multiple users. The training device 800 is structurally and operationally similar to training device 100 in FIGS. 1A-7C except that the upper segment 814*a* of the outer sleeve 802 culminates at a truncated tip 815. As shown in FIG. 8, this truncated tip 815 does not extend past the depth guide 804, and therefore during use, the truncated tip 815 is not inserted into any nostril of the user. Instead, prior to the first stage of operation, a user can position the device 800 to a first side of their head such that their hand and wrist are in similar positions as if the truncated tip 815 was placed in their first nostril. That is, a user can place the device 800 to the first side of their head at a position in which the truncated tip 815 is laterally aligned with the position of their first nostril and the depth guide 804 is laterally aligned with the position of their skin between their first and second nostrils. Likewise, prior to the second stage of operation, a user can position the device 800 to a second side of their head such that their hand and wrist are in similar positions as if the truncated tip 815 was placed in their second nostril. That is, a user can place the device 800 to the second side of their head at a position in which the truncated tip 815 is laterally aligned with the position of their second nostril and the depth guide 804 is laterally aligned with the position of their skin between their first and second nostrils. Once the user is familiar with the operational steps of the device 800, the device 800 can be returned, e.g., to a health care provider who may clean it (using sterilizing alcohol wipes or similar) and store it for the next user.

Figure 9B:
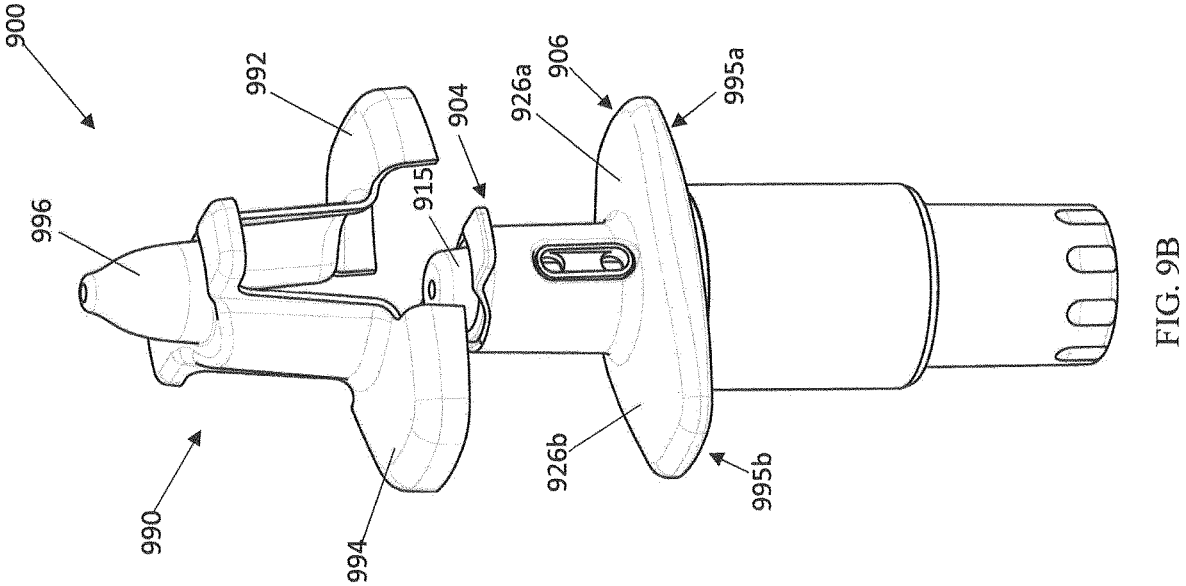
FIG. 9B is a partial exploded view of the device of FIG. 9A.
Figure 9A:
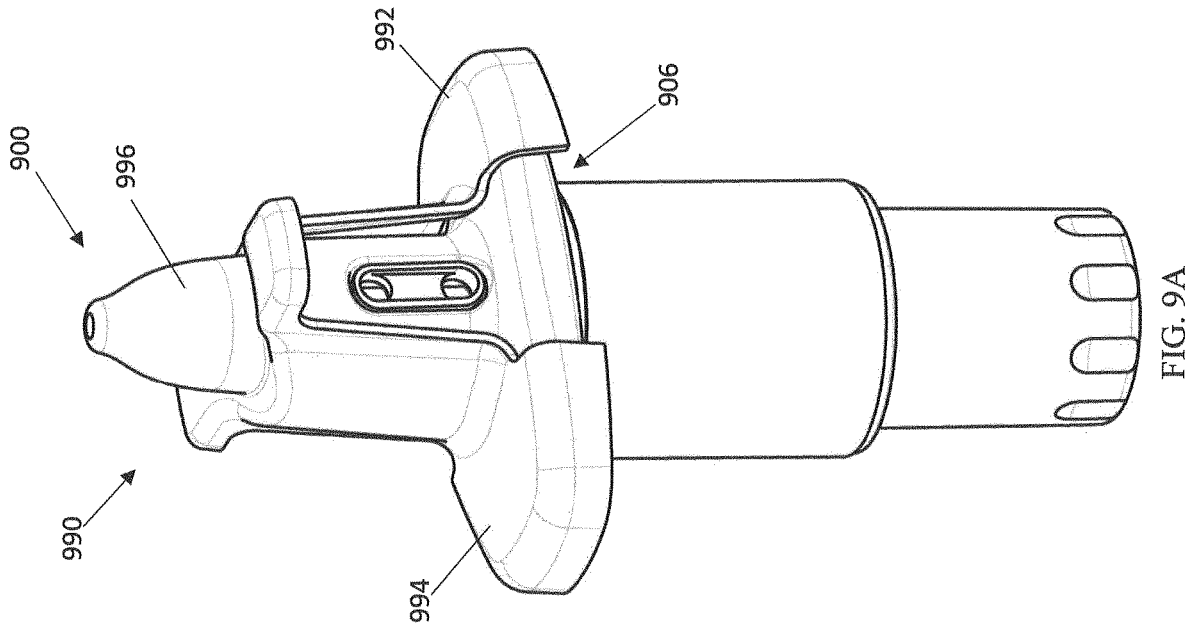
FIG. 9A is an isometric view of the device of FIG. 8, showing a protective hygiene cap coupled thereto.

FIGS. 9A and 9B illustrate another exemplary embodiment of a training device 900 that can be used multiple times by multiple users. The training device 900 is structurally and operational similar to training device 800 except that the device 900 includes a protective hygiene cap 990 that is selectively mateable with and removeable from the device 900. Prior to use of the device 900, the protective hygiene cap 990 can be placed over and mated to the tip 915 of the training device 900 such that the tip 915, depth guide 904, and the finger rest 906 are protected by the cap 990. The cap 990 includes two snapping arms 992, 994 that are configured to snap into position over the ends 995*a*, 995*b* of the opposing flanges 926*a*, 926*b* of the finger rest 906 to thereby secure the cap to the device 900.

As further shown, the cap 990 includes a tip 996 that shares the same profile as the tip 115 of training device 100 shown in FIGS. 1A-7C, such that when the cap 990 is coupled to the finger rest 906, the tip 996 can be similarly inserted into the nostrils of a user as discussed above. Therefore, when the cap is coupled to the device 900, the user can practice all the operational steps of the device 900, including insertion into the nostrils. However, in this illustrated embodiment, the training device 900 itself remains free from contact with the nose and fingertips of the user and therefore, the device 900 remains hygienically clean. When the user has practiced sufficiently and feels comfortable with the positioning and actuation process of the training device 900, a health care provider can remove and dispose of the cap 990 before storing the training device 900 for subsequent use by a different user.

Further, this training device can be provided with more than one protective hygiene cap 990. In such embodiments, once all caps have been exhausted, the device can be disposed of and replaced with a complete new device and corresponding protective hygiene caps. As a result, degradation of the actuation mechanism of the device can be managed by the number of caps supplied with the device.

This can prevent a user from using an overused device that does not provide the proper tactical experience during use. Moreover, using protective hygiene caps allows for fewer devices to be used and disposed of compared to those without protective hygiene caps.

While the hygiene cap 990 is primarily described with respect to the embodiments of FIGS. 8-9B, a person skilled in the art will understand that the hygiene cap 990 can likewise be used with the embodiments of FIGS. 1-7C, making any modifications that will ensure the appropriate fit of the hygiene cap 990.

The devices disclosed herein can be formed of one or more polymers, e.g. polycarbonate, that are known to those skilled in the art. In some embodiments, the first and second biasing elements can be formed of one or more metals such as spring steel.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a health care provider immediately prior to use. Those skilled in the art will appreciate that reconditioning of a device can utilize a variety of techniques for disassembly, cleaning/replacement, and reassembly. Use of such techniques, and the resulting reconditioned device, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user gripping a plunger of a device. Other spatial terms such as "front" and "rear" similarly correspond respectively to distal and proximal. It will be further appreciated that for convenience and clarity, spatial terms such as "vertical" and "horizontal" are used herein with respect to the drawings. However, devices are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such, the disclosure as explicitly set forth herein supersedes any conflicting material incorporated herein by reference.

The following is a non-exhaustive list of embodiments that may or may not be claimed.

1. A training device for simulating intranasal drug delivery, the device comprising:
    an outer sleeve having upper and lower portions;
    a locking sleeve coupled to the outer sleeve and partially extending therethrough;
    a core sleeve coupled to the locking sleeve and configured to axially slide within the outer and locking sleeves, the core sleeve having first and second sets of locking features; and
    a plunger operatively coupled to the core sleeve, the plunger being configured to selectively translate the core sleeve from an initial position to a first actuated position in response to the application of a first actuation force that exceeds a first force threshold, and the plunger being configured to translate the core sleeve from the first actuated position to a second actuated position in response to the application of a second actuation force that exceeds a second force threshold;
    wherein the first force threshold corresponds to a first spray threshold for releasing a first simulated dose of a drug and the second force threshold corresponds to a second spray threshold for releasing a second simulated dose of the drug, and
    wherein the device does not contain the drug.
2. The device of embodiment 1, further comprising a protective hygiene cap that is selectively mateable with and removable from the device.
3. The device of embodiment 1, wherein the first sets of locking features each include first and second flanges extending from an outer surface of the core sleeve and a first locking groove defined therebetween, and wherein the first locking groove is configured to retain the core sleeve in the first actuated position.

4. The device of embodiment 3, wherein the second sets of locking features each include third and fourth flanges extending from an outer surface of the core sleeve and a second locking groove defined therebetween, and wherein the second locking groove is configured to retain the core sleeve in the second actuated position.
5. The device of embodiment 4, wherein the locking sleeve comprises at least two snap arms, each snap arm having a protrusion extending from an inner surface thereof and toward the core sleeve, wherein each protrusion is configured to engage the first locking groove when the core sleeve is in the first actuated position and configured to engage the second locking groove when the core sleeve is the second actuated position.
6. The device of embodiment 1, wherein the plunger returns to a start position after the application of the first actuation force and after the application of the second actuation force.
7. The device of embodiment 1, further comprising an indicator rod disposed within the upper portion of the outer sleeve, and wherein the indicator rod is viewable through first and second indicator windows of the upper portion when the core sleeve is in the initial position.
8. The device of embodiment 7, wherein the core sleeve is configured to slide between indicator rod and the upper portion of the outer sleeve such that the core sleeve blocks the first indicator window when the core sleeve is in the first actuated position.
9. The device of embodiment 8, wherein the core sleeve blocks the first and second indicator windows when the core sleeve is in the second actuated position.
10. A training device for simulating intranasal drug delivery, the device comprising:
    an outer sleeve having upper and lower portions;
    a locking sleeve coupled to the outer sleeve and partially extending therethrough;
    a core sleeve coupled to the locking sleeve and configured to axially slide within the outer and locking sleeves, the core sleeve having first and second sets of locking features; and
    a plunger operatively coupled to the core sleeve, the plunger being configured to selectively translate the core sleeve from an initial position to a first actuated position that indicates the release of a first simulated dose of a drug, and the plunger being configured to translate the core sleeve from the first actuated position to a second actuated position that indicates the release of a second simulated dose of the drug;
    wherein the device does not contain a drug.
11. The device of embodiment 10, further comprising an indicator rod disposed within the upper portion of the outer sleeve, and wherein the indicator rod is viewable through first and second indicator windows of the upper portion when the core sleeve is in the initial position.
12. The device of embodiment 11, wherein the core sleeve is configured to slide between the indicator rod and the upper portion of the outer sleeve such that the core sleeve blocks the first indicator window when the core sleeve is in the first actuated position to thereby indicate the release of the first simulated dose of the drug.
13. The device of embodiment 12, wherein the core sleeve blocks the first and second indicator windows when the core sleeve is in the second actuated position to thereby indicate the release of the second simulated dose of the drug.
14. The device of embodiment 10, further comprising a protective hygiene cap that is selectively mateable with and removable from the outer sleeve.

15. The device of embodiment 10, wherein the first sets of locking features each include first and second flanges extending from an outer surface of the core sleeve and a first locking groove defined therebetween, and wherein the first locking groove is configured to retain the core sleeve in the first actuated position.

16. The device of embodiment 15, wherein the second sets of locking features each include third and fourth flanges extending from an outer surface of the core sleeve and a second locking groove defined therebetween, and wherein the second locking groove is configured to retain the core sleeve in the second actuated position.

17. The device of embodiment 16, wherein the locking sleeve comprises at least two snap arms, each snap arm having a protrusion extending from an inner surface thereof and toward the core sleeve, wherein each protrusion is configured to engage the first locking groove when the core sleeve is in the first actuated position and configured to engage the second locking groove when the core sleeve is the second actuated position.

18. The device of embodiment 10, wherein the plunger returns to a start position after the application of the first actuation force and after the application of the second actuation force.

19. A training device for simulating intranasal drug delivery, the device comprising:

an outer sleeve having upper and lower portions;

a locking sleeve coupled to the outer sleeve and partially extending therethrough;

a core sleeve coupled to the locking sleeve and configured to axially slide within the outer and locking sleeves; and a plunger operatively coupled to the core sleeve and configured to axially translate relative to the outer sleeve to selectively slide the core sleeve in a first axial direction from a start position to a first axial position and from the first axial position to a second axial position, the plunger being further configured to rotate relative to the outer sleeve between an initial position and an actuated radial position;

wherein, when the core sleeve is in the second axial position, rotation of the plunger from the initial position to the actuated radial position resets the core sleeve to the start position such that the core sleeve can axially translate back to the first and second axial positions.

20. The device of embodiment 19, further comprising a protective hygiene cap that is selectively mateable with and removable from the device.

21. The device of embodiment 19, wherein the core sleeve is configured to be repeatedly reset.

22. The device of embodiment 19, further comprising a first biasing element that biases the plunger to the initial position until a rotational force is applied to the plunger that overcomes a rotational biasing force of the first biasing element and thereby rotates the plunger in a first rotational direction.

23. The device of embodiment 22, wherein release of the rotational force allows the first biasing element to rotate the plunger in a second, opposite rotational direction to allow the plunger to return to the initial position.

24. The device of embodiment 22, further comprising a second biasing element that biases the core sleeve to the start position until an axial force is applied to the core sleeve that overcomes an axial biasing force of the second biasing element and thereby translates the core sleeve in the first axial direction.

25. The device of embodiment 22, wherein, when the core sleeve is in the second axial position, rotation of the plunger in the first rotational direction causes the core sleeve to rotate and disengage from the locking sleeve.

26. The device of embodiment 25, wherein, when the core sleeve is disengaged from the locking sleeve, the second biasing element forces the core sleeve in a second, opposite axial direction from the second axial position toward the start position.

27. The device of embodiment 26, wherein release of the rotational force allows the first biasing element to rotate the plunger in a second, opposite rotational direction until the plunger reaches the initial position, and wherein rotation of the plunger in the second rotational direction rotates the core sleeve back to the start position.

28. A method for simulating intranasal drug delivery, the method comprising:

depressing a plunger operatively coupled to a core sleeve of a training device to axially translate the core sleeve in a first axial direction from a start position to a first actuated position, the first actuated position being associated with the completion of the release of a first simulated dose of a drug;

depressing the plunger to axially translate the core sleeve in the first axial direction from the first actuated position to a second actuated position, the second actuated position being associated with the completion of the release of a second simulated dose of the drug; and rotating the plunger to reset the core sleeve to the start position to thereby allow the core sleeve to axially translate back to the first and second actuated positions;

wherein the device does not contain a drug.

29. The method of embodiment 28, further comprising, prior to depression of the plunger when the core sleeve is in the start position, inserting a portion of the device into a first nostril.

30. The method of embodiment 29, further comprising, prior to depression of the plunger when the core sleeve is in the first actuated position, removing the device from the first nostril and inserting the portion of the device into a second nostril.

31. The method of embodiment 28, wherein rotation of the plunger comprises:

applying a rotational force to the plunger to rotate the plunger in a first rotational direction to thereby move the plunger from an initial radial position to an actuated radial position; and releasing the rotational force to allow the plunger to rotate in a second, opposite radial direction and return to the initial radial position.

32. The method of embodiment 29, wherein, prior to depression of the plunger, an indicator rod disposed within an outer sleeve of the training device is viewable through first and second indicator windows of the outer sleeve.

33. The method of embodiment 32, wherein depressing the plunger to axially translate the core sleeve to the first actuated position causes the core sleeve to translate in a distal direction between the indicator rod and the outer sleeve to thereby block the indicator rod from being viewable through the first indicator window to indicate the completion of the release of the first simulated dose of the drug.

34. The method of embodiment 33, wherein depressing the plunger to axially translate the core sleeve to the second actuated position causes the core sleeve to further translate in the distal direction between the indicator rod and the outer sleeve to thereby block the indicator rod from being viewable through the first and second indicator windows to indicate the completion of the release of the second simulated dose of the drug.

35. The method of embodiment 34, wherein rotating the plunger causes the core sleeve to translate back in a proximal direction between the indicator rod and the outer sleeve to thereby unblock the first and second indicator windows such that the indicator rod is viewable therethrough to indicate that the core sleeve is reset.

What is claimed is:

1. A training device for simulating intranasal drug delivery, the device comprising:

an outer sleeve having upper and lower portions;

a locking sleeve coupled to the outer sleeve and partially extending therethrough;

a core sleeve coupled to the locking sleeve and configured to axially slide within the outer and locking sleeves, the core sleeve having first and second sets of locking features; and a plunger operatively coupled to the core sleeve, the plunger being configured to selectively translate the core sleeve from an initial position to a first actuated position in response to the application of a first actuation force that exceeds a first force threshold, and the plunger being configured to translate the core sleeve from the first actuated position to a second actuated position in response to the application of a second actuation force that exceeds a second force threshold;

wherein the first force threshold corresponds to a first spray threshold for releasing a first simulated dose of a drug and the second force threshold corresponds to a second spray threshold for releasing a second simulated dose of the drug; and wherein the device does not contain the drug.

2. A training device for simulating intranasal drug delivery, the device comprising:

an outer sleeve having upper and lower portions;

a locking sleeve coupled to the outer sleeve and partially extending therethrough;

a core sleeve coupled to the locking sleeve and configured to axially slide within the outer and locking sleeves, the core sleeve having first and second sets of locking features; and a plunger operatively coupled to the core sleeve, the plunger being configured to selectively translate the core sleeve from an initial position to a first actuated position that indicates the release of a first simulated dose of a drug, and the plunger being configured to translate the core sleeve from the first actuated position to a second actuated position that indicates the release of a second simulated dose of the drug;

wherein the device does not contain a drug.

3. The device of claim 1, further comprising an indicator rod disposed within the upper portion of the outer sleeve, and wherein the indicator rod is viewable through first and second indicator windows of the upper portion when the core sleeve is in the initial position.

4. The device of claim 3, wherein the core sleeve is configured to slide between the indicator rod and the upper portion of the outer sleeve such that the core sleeve blocks the first indicator window when the core sleeve is in the first actuated position to thereby indicate the release of the first simulated dose of the drug.

5. The device of claim 4, wherein the core sleeve blocks the first and second indicator windows when the core sleeve is in the second actuated position to thereby indicate the release of the second simulated dose of the drug.

6. The device of claim 1, wherein the first sets of locking features each include first and second flanges extending from an outer surface of the core sleeve and a first locking groove defined therebetween, and wherein the first locking groove is configured to retain the core sleeve in the first actuated position.

7. The device of claim 1, wherein the second sets of locking features each include third and fourth flanges extending from an outer surface of the core sleeve and a second locking groove defined therebetween, and wherein the second locking groove is configured to retain the core sleeve in the second actuated position.

8. The device of claim 1, wherein the locking sleeve comprises at least two snap arms, each snap arm having a protrusion extending from an inner surface thereof and toward the core sleeve, wherein each protrusion is configured to engage the first locking groove when the core sleeve is in the first actuated position and configured to engage the second locking groove when the core sleeve is in the second actuated position.

9. The device of claim 1, wherein the plunger returns to a start position after the application of the first actuation force and after the application of the second actuation force.

10. A training device for simulating intranasal drug delivery, the device comprising:

an outer sleeve having upper and lower portions;

a locking sleeve coupled to the outer sleeve and partially extending therethrough;

a core sleeve coupled to the locking sleeve and configured to axially slide within the outer and locking sleeves; and a plunger operatively coupled to the core sleeve and configured to axially translate relative to the outer sleeve to selectively slide the core sleeve in a first axial direction from a start position to a first axial position and from the first axial position to a second axial position, the plunger being further configured to rotate relative to the outer sleeve between an initial position and an actuated radial position;

wherein, when the core sleeve is in the second axial position, rotation of the plunger from the initial position to the actuated radial position resets the core sleeve to the start position such that the core sleeve can axially translate back to the first and second axial positions.

11. The device of claim 10, further comprising a protective hygiene cap that is selectively mateable with and removable from the device, preferably removable from the outer sleeve.

12. The device of claim 10, wherein the core sleeve is configured to be repeatedly reset.

13. The device of claim 10, further comprising a first biasing element that biases the plunger to the initial position until a rotational force is applied to the plunger that overcomes a rotational biasing force of the first biasing element and thereby rotates the plunger in a first rotational direction.

14. The device of claim 13, wherein release of the rotational force allows the first biasing element to rotate the plunger in a second, opposite rotational direction to allow the plunger to return to the initial position.

15. The device of claim 13, further comprising a second biasing element that biases the core sleeve to the start position until an axial force is applied to the core sleeve that overcomes an axial biasing force of the second biasing element and thereby translates the core sleeve in the first axial direction.

16. The device of claim 13, wherein, when the core sleeve is in the second axial position, rotation of the plunger in the first rotational direction causes the core sleeve to rotate and disengage from the locking sleeve.

17. The device of claim 15, wherein, when the core sleeve is disengaged from the locking sleeve, the second biasing element forces the core sleeve in a second, opposite axial direction from the second axial position toward the start position.

18. The device of claim 13, wherein release of the rotational force allows the first biasing element to rotate the plunger in a second, opposite rotational direction until the plunger reaches the initial position, and wherein rotation of the plunger in the second rotational direction rotates the core sleeve back to the start position.

19. A method for simulating intranasal drug delivery, the method comprising:

depressing a plunger operatively coupled to a core sleeve of a training device to axially translate the core sleeve in a first axial direction from a start position to a first actuated position, the first actuated position being associated with the completion of the release of a first simulated dose of a drug;

depressing the plunger to axially translate the core sleeve in the first axial direction from the first actuated position to a second actuated position, the second actuated position being associated with the completion of the release of a second simulated dose of the drug; and rotating the plunger to reset the core sleeve to the start position to thereby allow the core sleeve to axially translate back to the first and second actuated positions; wherein the device does not contain a drug.

20. The method of claim 19, further comprising, prior to depression of the plunger when the core sleeve is in the start position, inserting a portion of the device into a first nostril.

21. The method of claim 20, further comprising, prior to depression of the plunger when the core sleeve is in the first actuated position, removing the device from the first nostril and inserting the portion of the device into a second nostril.

22. The method of claim 19, wherein rotation of the plunger comprises: applying a rotational force to the plunger to rotate the plunger in a first rotational direction to thereby move the plunger from an initial radial position to an actuated radial position; and releasing the rotational force to allow the plunger to rotate in a second, opposite radial direction and return to the initial radial position.

23. The method of claims 19, wherein, prior to depression of the plunger, an indicator rod disposed within an outer sleeve of the training device is viewable through first and second indicator windows of the outer sleeve.

24. The method of claim 23, wherein depressing the plunger to axially translate the core sleeve to the first actuated position causes the core sleeve to translate in a distal direction between the indicator rod and the outer sleeve to thereby block the indicator rod from being viewable through the first indicator window to indicate the completion of the release of the first simulated dose of the drug.

25. The method of claim 24, wherein depressing the plunger to axially translate the core sleeve to the second actuated position causes the core sleeve to further translate in the distal direction between the indicator rod and the outer sleeve to thereby block the indicator rod from being viewable through the first and second indicator windows to indicate the completion of the release of the second simulated dose of the drug.

26. The method of claim 25, wherein rotating the plunger causes the core sleeve to translate back in a proximal direction between the indicator rod and the outer sleeve to thereby unblock the first and second indicator windows such that the indicator rod is viewable therethrough to indicate that the core sleeve is reset.

* * * * *